US011298361B2

(12) United States Patent
Chipkin et al.

(10) Patent No.: US 11,298,361 B2
(45) Date of Patent: Apr. 12, 2022

(54) FUSED BENZAZEPINES FOR TREATMENT OF TOURETTE'S SYNDROME

(71) Applicant: EMALEX BIOSCIENCES, INC., North Chicago, IL (US)

(72) Inventors: Richard E. Chipkin, Bethesda, MD (US); Rudolf Kwan, Summit, NJ (US)

(73) Assignee: EMALEX BIOSCIENCES, INC., Chicago, IL (US)

( * ) Notice: Subject to any disclaimer, the term of this patent is extended or adjusted under 35 U.S.C. 154(b) by 415 days.

(21) Appl. No.: 14/414,368

(22) PCT Filed: Jul. 12, 2013

(86) PCT No.: PCT/US2013/050337
§ 371 (c)(1),
(2) Date: Jan. 12, 2015

(87) PCT Pub. No.: WO2014/012034
PCT Pub. Date: Jan. 16, 2014

(65) Prior Publication Data
US 2015/0164911 A1 Jun. 18, 2015

Related U.S. Application Data

(60) Provisional application No. 61/671,044, filed on Jul. 12, 2012.

(51) Int. Cl.
A61K 31/55 (2006.01)
A61K 45/06 (2006.01)

(52) U.S. Cl.
CPC ............. A61K 31/55 (2013.01); A61K 45/06 (2013.01)

(58) Field of Classification Search
CPC .................................................. A61K 31/55
See application file for complete search history.

(56) References Cited

U.S. PATENT DOCUMENTS

| 4,477,378 | A | 10/1984 | Gold et al. |
| 4,973,586 | A | 11/1990 | Berger et al. |
| 5,302,716 | A | 4/1994 | Berger et al. |
| 6,132,724 | A | 10/2000 | Blum |
| 9,949,983 | B2 | 4/2018 | Chipkin |
| 2003/0109532 | A1 | 6/2003 | Sonesson et al. |
| 2010/0273767 | A1 | 10/2010 | Wang et al. |
| 2011/0206782 | A1 | 8/2011 | Zhang |
| 2011/0262442 | A1 | 10/2011 | Hamilton et al. |

FOREIGN PATENT DOCUMENTS

| CA | 2465869 | 5/2003 |
| JP | 10-509139 | 9/1998 |
| WO | WO1993001702 A1 | 1/1993 |
| WO | WO1993013073 A1 | 7/1993 |
| WO | WO-95/25102 A1 | 9/1995 |
| WO | WO 1996/013257 A1 | 5/1996 |
| WO | WO-99/021540 A2 | 5/1999 |
| WO | WO 03/039468 A2 | 5/2003 |
| WO | WO2011057199 A1 | 3/2011 |
| WO | WO 2012/033874 | 3/2012 |

OTHER PUBLICATIONS

Braun, A. et al. "Selective D-1 dopamnie receptor agonist effects in hyperkinetic extrapyramidal disorders," Journal of Neurology, Neurosurgery and Psychiatry (1989) vol. 52, pp. 631-635.
Cianchetti, C. et al. "Pergolide improvement in neuroleptic-resistant Tourette cases: various mechanisms causing tics," Neurol. Sci. (2005) vol. 26, No. 2, pp. 137-139.
Dursun, S.M. et al., "Similarities in the pharmacology of spontaneous and DOI-induced head-shakes suggest $5HT_{2A}$ receptors are active under physiological conditions," Psychopharmacology (1996) vol. 128, No. 2, pp. 198-205.
Gilbert, D.L et al. "Tic reduction with pergolide in a randomized controlled trial in children," Neurology (2003) vol. 60, No. 4, pp. 606-611.
Gilbert, D.L. et al. "Tourette's syndrome improvement with pergolide in a randomized, double-blind crossover trial," Neurology (2000) vol. 54, No. 6, pp. 1310-1315.
Griesemer, D.A. "Pergolide in the management of Tourette Syndrome," Journal of Child Neurology (1997) vol. 12, No. 6, pp. 402-403.
Lipinski, J.F. et al. "Dopamine agonist treatment of Tourette disorder in children: Results of an open-label trial of pergolide," Movement Disorders (1997) vol. 12, No. 3, pp. 402-407.
Patent Examination Report No. 1 from Australian Patent Application No. 2013289922, dated Nov. 24, 2015 in 5 pages.
Scahiil, L. et al. "Pharmacologic treatment of tic disorders," Child Adolesc. Psychiatr. Clin. N. Am. (2000) vol. 9, No. 1, pp. 99-117.
McCreary, Andrew C. et al., The thyrotrophin-releasing hormone analogue MK771 induces tic-like behaviors: the effects of dopamine $D_1$ and $D_2$ ; receptor antagonists, European Journal of Pharmacology, (1999) vol. 369, pp. 1-9.
Qiang L. et al., "Discovery of new SCH 39166 analogs as potent and selective dopamine D1 receptor antagonists", Bioorganic & Medicinal Chemistry Letters, Pergamon, Amsterdam, NL, vol. 20, No. 3, Feb. 1, 2010, pp. 836-840.
Office Action and Examination Search Report in Canadian Application No. 2,879,020, dated Feb. 18, 2016, in 3 pages.
Kurlan, "Tourette's Syndrome" The New England Journal of Medicine 363:2332-2338, 2010.
Romach et al., "Attenuation of the euphoric effects of cocaine by the dopamine D1/D5 antagonist ecopipam (SCH 39166)" Archives of General Psychiatry, 1999, 56(12): 1101-1106, Dec. 1999.

(Continued)

Primary Examiner — Yong S. Chong
(74) Attorney, Agent, or Firm — Marshall, Gerstein & Borun LLP

(57) ABSTRACT

The present invention encompasses methods of treating a subject who has been diagnosed as having a tic disorder or a movement disorder. The tic disorder can be Tourette's Syndrome, and the methods can include the steps of: (a) identifying a subject in need of treatment; and (b) administering to the subject a therapeutically effective amount of a composition comprising a D1/D5 receptor antagonist, a D1/D5 receptor partial agonist, or a mixture thereof. For example, the D1/D5 receptor antagonist can be ecopipam or a pharmaceutically acceptable salt, solvate, hydrate, prodrug, structural analog, metabolite, or polymorph thereof.

21 Claims, 1 Drawing Sheet

(56) References Cited

OTHER PUBLICATIONS

International Search Report and Written Opinion of the International Searching Authority for PCT/US2013/050337, dated Nov. 14, 2013.
International Search Report for PCT/US2013/050337, published on Jan. 16, 2014.
Second Office Action issued in Chinese Patent Application No. 2013800369039, dated Nov. 28, 2016, in 11 pages.
Communication pursuant to Article 94(3) EPC in European Application No. 13815988.4, dated Apr. 19, 2017, in 4 pages.
Dunlap, Lynn, "TSA: Psyadon to collaborate on drug trial", https://missouritsa.org/2011/05/12/tsa-psyadon-to-collaborate-on-drug-trial/, May 12, 2011, Missouri.
Arnt et al., The citalopram/5HTP-induced head shake syndrome is correlated to 5-HT2 receptor affinity and also influenced by other transmitters., Acta Pharmacol Toxicol (Copenh) 55(5)-36372.
Beaulieu and Gainetdinov, The Physiology, Signaling, and Pharmacology of Dopamine Receptors, Pharmacol Rev 63(1):182-217 (2011).
Bedard and Pycock, The 'wet dog shake' behaviour in the rat and 5-hydroxytryptamine, Br J Pharmacol 59(3): 450P-451P(1977).
Berge, et al., Pharmaceutical Salts, Journal of Pharmaceutical Sciences 66(1): 1-19 (1977).
Bonnier et al., Ketanserin treatment of Tourette's Syndrome in children, American Journal of Psychiatry 156 (7):1122a-1123 (1999).
Borowski et al., Blood Pressure Response to Thyrotropin-Releasing Hormone in Euthyroid Subjects, J Clin Endocrinol Metab 58(1):197-200 (1984).
Castellano et al., Post-training dopamine receptor agonists and antagonists affect memory storage in mice irrespective of their selectivity for D1 or D2 receptors. Behav Neural Biol 56(3):283-91 (1991).
Cavanna et al., The Behavioral Spectrum of Gilles de la Tourette Syndrome, Journal of Neuropsychiatry and Clinical Neurosciences 21-13 (2009).
Chipkin et al., Pharmacological Profile of SCH39166: A Dopamine D1 Selective Benzonaphthazepine With Potential Antipsychotic Activity, Journal of Pharmacology and Experimental Therapeutics 247(3): 1093-1102 (1988).
Civelli et al., Molecular Diversity of the Dopamine Receptors, Annual Review of Pharmacology and Toxicology 33:281-307 (1993).
Corne et al., A Method for Assessing the Effects of Drugs on the Central Actions of 5-Hydroxytryptamine, Brit J Pharmacol 20: 106-120 (1963).
Duffy et al., In vivo autoradiography of [3H]SCH 39166 in rat brain: selective displacement by D1/D5 antagonists, Journal of Chemical Neuroanatomy 19:41-46 (2000).
Emilien et al., Dopamine receptors—physiological understanding to therapeutic intervention potential, Pharmacology and Therapeutics 84:133-156 (1999).
Felling and Singer, Neurobiology of Tourette Syndrome: Current Status and Need for Further Investigation, Journal of Neuroscience 31(35): 12387-12395 (2011).
Fenu et al., Differential involvement of dopamine D1 receptors in morphine- and lithium-conditioned saccharin avoidance Physiology & Behavior 96: 73-77 (2009).
Gobira et al., Animal models for predicting the efficacy and side effects of antipsychotic drugs, Revista Brasileira de Psiquiatria 35: S132-S139 (2013).
Haile et al., The dopamine D1 receptor agonist SKF-82958 serves as a discriminative stimulus in the rat, European Journal of Pharmacology 388: 125-131 (2000).
Himle et al., Establishing the feasibility of direct observation in the assessment of tics in children with chronic tic disorders, Journal of Applied Behavior Analysis 39: 429-440 (2006).
Jankovic J., Tourette's Syndrome, The New England Journal of Medicine, 345(16): 1184-1192 (2001).

Karlsson et al., Evaluation of SCH 39166 as PET ligand for central D1 dopamine receptor binding and occupancy in man, Psychopharmacology (Berl) 121(3):300-308 (1995).
Karlsson et al., Lack of apparent antipsychotic effect of the D1-dopamine receptor antagonist SCH39166 in acutely ill schizophrenic patients, Psychopharmacology (Berl) 121(3): 309-316 (1995).
Karson et al., Eye-blink rate in Tourette's syndrome, J Nerv Ment Dis 173(9): 566-569 (1985).
Kenney et al., Tourette's Syndrome, American Family Physician 77(5):651-658 (2008).
Leckman et al., Course of Tic Severity in Tourette Syndrome: The First Two Decades, Pediatrics 102:14-19 (1998).
Markham and Benfield, Pergolide: A Review of its Pharmacology and Therapeutic Use in Parkinson's Disease, CNS Drugs 7(4):328-340 (1997).
McQuade et al., [3H]SCH 39166, a new D1-selective radioligand: in vitro and in vivo binding analyses, Journal of Neurochemistry 57(6):2001-10 (1991).
McQuade et al., In vivo binding of SCH 39166: a D-1 selective antagonist, J Pharmacol Exp Ther 257(1) 42-49 (1991).
Müller N., Tourette's syndrome: clinical features, pathophysiology, and therapeutic approaches, Dialogues Clin Neurosci. 9(2):161-71 (2007).
Ravin, L., "Preformulation," Remington's Pharmaceutical Sciences, 17th ed., Mack Publishing Company, Easton, Pa., 1985, Chapter 76, pp. 1409-1423.
Schindler et al., Serotonergic and dopaminergic distinctions in the behavioral pharmacology of ($\pm$)-1-(2,5-dimethoxy-4-iodophenyl)-2-aminopropane (DOI) and lysergic acid diethylamide (LSD), Pharmacol Biochem Behav 101 (1): 69-76 (2012).
Shah et al., (+/−)-(N-alkylamino)benzazepine analogs: novel dopamine D1 receptor antagonists, Journal of Medicinal Chemistry 38(21):4284-93 (1995).
Staley et al., Tourette disorder: a cross-cultural review, Comprehensive Psychiatry 38(1): 6-16 (1997).
Starr and Starr, Differential effects of dopamine D1 and D2 agonists and antagonists on velocity of movement, rearing and grooming in the mouse. Implications for the roles of D1 and D2 receptors, Neuropharmacology 25(5): 45563 (1986).
Starr and Starr, Grooming in the mouse is stimulated by the dopamine D1 agonist SKF 38393 and by low doses of the D1 antagonist SCH 23390, but is inhibited by dopamine D2 agonists, D2 antagonists and high doses of SCH 23390. Pharmacology Biochemistry & Behavior 24(4):837-9 (1986).
Swerdlow and Sutherland, Using animal models to develop therapeutics for Tourette Syndrome, Pharmacology and Therapeutics 108(3):281-93 (2005).
Taylor et al., Dopamine receptor modulation of repetitive grooming actions in the rat: potential relevance for Tourette syndrome, Brain Res 1322:92-101 (2010).
Weisman et al., Systematic review: pharmacological treatment of tic disorders-efficacy of antipsychotic and alpha-2 adrenergic agonist agents, Neuroscience and Biobehavioral Reviews 37(6):1162-71 (2013).
Schrieber et al., (1-(2,5-dimethoxy-4 iodophenyl)-2-aminopropane)-induced head-twitches in the rat are mediated by 5-hydroxytryptamine (5-HT) 2A receptors: modulation by novel 5-HT2A/2C antagonists, D1 antagonists and 5-HT1A agonists, J Pharmacol Exp Ther 273(1):101-112 (1995).
Ashurst, John et al., Developmental and Persistent Developmental Stuttering: An Overview for Primary Care Physicians, Journal of American Osteopathic Associations, 111, 576-580, 2011.
Astrup et al., "Randomized Controlled Trials of the D1/D5 Antagonist Ecopipam for Weight Loss in Obese Subjects," Obesity, 15(7):1717-1731 (2007).
Blomgren, Michael, Behavioral Treatments for Children and Adults Who Stutter: a Review, Psychol. Res. Behav. Management, 6:9-19, 2013.
Bothe, AK et al., Stuttering Treatment Research 1970-2005. I: Systematic Review Incorporating Trial Quality Assessment of Behavioral, Cognitive, and Related Approaches, American Journal of Speech-Language Pathology, 15:321-341, 2006.

(56) References Cited

OTHER PUBLICATIONS

Boyd, A et al., Pharmacological Agents for Developmental Stuttering in Children and Adolescents: A Systemic Review, J. Clin. Psychopharmacol., 31(6):740-744, 2011.

Brett et al., "The Genetic Susceptibility to Gilles de la Tourette Syndrome in a Large Multiple Affected British Kindred: Linkage Analysis Excludes a Role for the Genes Coding for Dopamine D1, D2, D3, D4, D5 Receptors, Dopamine Beta Hydroxylase, Tyrosinase, and Tyrosine Hydroxylase," Biol. Psychiatry, 37(8):533-540 (1995).

Buchel, Christian et al., What Causes Stuttering?, PLoS Biology, 2(2):159-163, 2004.

Communication pursuant to Article 94(3) EPC in European Application No. 13815988.4, dated Jun. 25, 2018.

Costa, Daniel et al., Stuttering: an Update for Physicians, Canadian Medical Association Journal, 162:1849-1855, 2000.

De Beaurepaire et al., "An Open Trial of the $D_1$ Antagonist SCH 39166 in Six Cases of Acute Psychotic States," Psychopharmacology, 121:323-327 (1995).

Den Boer et al., "Differential Effects of the D1-DA Receptor Antagonist SCH39166 on Positive and Negative Symptoms of Schizophrenia," Psychopharmacology, 121:317-322 (1995).

Diagnostic and Statistical Manual of Mental Disorders [DSM-IV-TR], Fourth Edition, American Psychiatric Association (2000). Table of Contents.

Duffy et al., "In viva autoradiography of [$^{3H}$]SCH 39166 in rat brain: Selective displacement by D1/D5 antagonists," J. Chem. Neuroanatomy, 19:41-46 (2000).

Ecopipam, Wikipedia, Apr. 26, 2013, Retrieved from the Internet: URL:https://en.wikipedia.org/wiki/Ecopipam, 4 Pages.

European Search Report issued in connection with European Patent Application No. 14854586.6, dated Sep. 5, 2017, 10 pages.

Extended European Search Report for Application No. 13815988.4, dated Nov. 3, 2015.

First Office Action issued in Chinese Patent Application No. 2013800369039, dated Jan. 6, 2016.

Fourth Office Action issued in Chinese Patent Application No. 2013800369039, dated May 9, 2018.

Gelernter et al., "Exclusion of close Linkage of Tourette's Syndrome to D1 Dopamine Receptor," Am. J. Psychiatry, 150(3):449-453 (1993).

Gilbert et al., "A D1 Receptor Antagonist, Ecopipam, for Treatment of Tics in Tourette Syndrome," Clinical Neuropharmacology, 37(1):26-30 (2014).

Grant et al., "A Single-Blind Study of 'As-Needed' Ecopipam for Gambling Disorder," Annals of Clinical Psychiatry, 26(3):179-186 (2014).

Haney et al., "Controversies in Translational Research: Drug self-administration," Psychopharmacology, 199(3):403-419 (2008).

Ingham, Roger et al., Towards a Functional Neural Systems Model of Developmental Stuttering, J. Fluency Disord., 28(4):297-317, 2003.

International Preliminary Reporton Patentability for Application No. PCT/US2014/061080, dated Apr. 19, 2016.

International Search Report and Written Opinion for Application No. PCT/US2014/061080, dated Dec. 24, 2014.

Jankovic et al., "Tourette's Syndrome and the Law," J. Neuropsychiatry Clin. Neurosci, 18(1):86-95 (2006).

Kraft, SJ et al., Genetic Bases of Stuttering: The State of the Art, 2011, Folia Phoniatr Logop, 64(1):34-47, 2012.

Leckman et al., "Tic Disorders: When Habit Forming Neural Systems Form Habits of Their Own?" Chinese Medical Journal (Taipei), 64:669-692 (2001).

Maguire, G. et al., Exploratory Randomized Clinical Study of Pagoclone in Persistent Developmental Stuttering: The Examining Pagoclone for Persistent Developmental Stuttering Study., J. Clin. Psychopharmacol. 30:48-56, 2010.

Maguire, Gerald et al., Alleviating Stuttering with Pharmacological Interventions, Expert Opinion on Pharmacotherapy, vol. 5, No. 7, 1565-1571, Jan. 2004.

Maguire, Gerald et al., Risperidone for the Treatment of Stuttering, Journal of Clinical Psychopharmacology, vol. 20, No. 4, 479-482, Aug. 2000.

Mozos-Ansorena et al., "Stuttering Treated with Olanzapine: A Case Report," Aetas Esp Psiquiatr, 40(4):231-233 (2012).

Nann-Vernotica et al., "Repeated Administration of the $D_{1/5}$ Antagonist Ecopipan Fails to Attenuate the Subjective Effects of Cocaine," Psychopharmacology, 155:338-347 (2001).

Newbury, D.F. et al., Genetic Advances in the Study of Speech and Language Disorders, Neuron, 68:309-320, 2010.

Notice of Final Rejection for Japanese Application No. 2015-521856, dated Nov. 16, 2016.

Notice of Final Rejection for Korean Application No. 10-2015-7001403, dated Jun. 28, 2016.

Notice of Preliminary Rejection for Korean Application No. 10-2015-7001403, dated Oct. 6, 2016.

Notice of Reasons for Rejection for Japanese Application No. 2015-521856, dated Nov. 30, 2015.

Notice of Reasons for Rejection for Japanese Application No. 2016-524108, dated Jun. 27, 2018.

Office Action and Examination Search Report in Canadian Application No. 2,879,020, dated Jul. 14, 2017.

Office Action and Examination Search Report in Canadian Application No. 2,879,020, dated Mar. 26, 2019.

Office Action and Examination Search Report in Canadian Application No. 2,879,020, dated Oct. 25, 2016.

Office Action for Israeli Application No. 236403, dated Apr. 9, 2018.

Office Action for Israeli Application No. 236403, dated Jul. 12, 2017.

Pettersson, Ingrid et al., A Study on the Contribution of the 1-Phenyl Substituent to the Molecular Electrostatic Potentials of Some Benzazepines in Relation to Selective Dopamine D-1 Receptor Activity, J. Med. Chem., vol. 35, 502-507, 1992.

Phelps, "Tourette's Disorder: Genetic Update, Neurological Correlates, and Evidence-Based Interventions," School Psychology Quarterly, 23(2):282-289 (2008).

Prasse, Jane et al., Stuttering: An Overview, American Family Physician, 77:1271-1276, 2008.

Raz, "Translational Attention: From Experiments in the Lab to Helping the Symptoms of Individuals with Tourette's Syndrome," Consciousness and Cognition, (21):1591-1594 (2012).

Reagan-Shaw et al., "Dose translation from animal to human studies revisited," FASEB Journal: Official Publication of the Federation of American Societies for Experimental Biology, 22(3):659-661 (2008).

Risperidone, Wikipedia, Mar. 31, 2017, Retrieved from the Internet: URL:https://en.wikipedia.org/wiki/Risperidone, 17 Pages.

*Sanofi v. Glenmark Pharmaceuticals, Inc.*, USA 204 F.Supp. 3d 665 (2016).

*Sanofi v. Watson Laboratories, Inc.*, 875 F.3d 636 (2017).

Shaygannejad Shaygannejad, Vahid et al., Olanzapine Versus Haloperidol: Which Can Control Stuttering Better?, Int J Prev Med. 4(Suppl 2):S270-273, 2013.

Shin et al., "Interpretation of Animal Dose and Human Equivalent Dose for Drug Development," The Journal of Korean Oriental Medicine, 31(3):1-7 (2010).

Singer et al., "Abnormal dopamine uptake sites in postmortem striatum from patients with Tourette's syndrome," Ann. Neurol., 30:558-562 (1991).

Third Office Action issued in Chinese Patent Application No. 2013800369039, dated Aug. 21, 2017.

VanHole, Nicholas. Shared Consciousness: A Social History of Tourette Syndrome and its Treatments. University of Montana. ScholarWorks at University of Montana. Theses, Dissertations, Professional Papers. 2012, 123 pages.

Zypadhera, European Medicines Agency, Apr. 25, 2014, XP002769139, 7 Pages.

"Acute Oral and Intraperitoneal Toxicity Studies of SCH 39166 (HCI) in Mice", Report No. P-5326, Study No. 88089, 88090 (Oct. 24, 1988).

"Acute Oral and Intraperitoneal Toxicity Studies of SCH 39166 (HCI) in Rats", Report No. P-5325, Study No. 88087, 88088 (Oct. 24, 1988).

(56) References Cited

OTHER PUBLICATIONS

European Patent Application No. 13815988.4, Communication Pursuant to Article 94(3) EPC, dated Jul. 11, 2019.
Godar et al., Animal models of tic disorders: A translational perspective, J. Neurosci. Methods, 238:54-69 (Dec. 2014).
Hayslett et al., Effects of donepezil, nicotine and haloperidol on the central serotonergic system in mice: implications for Tourette's syndrome, Pharmacol. Biochem. Behav., 81(4):879-86 (Aug. 2005).
Hollis et al., Clinical effectiveness and patient perspectives of different treatment strategies for tics in children and adolescents with Tourette syndrome: a systematic review and qualitative analysis, Health Technology Assessment, vol. 20, Issue 4, 496pp (Jan. 2016).
Marek, Behavioral evidence for mu-opioid and 5-HT2A receptor interactions, Eur. J. Pharmacol., 474(1):77-83 (Aug. 2003).
Yamada et al., Acute immobilization stress reduces (+/−)DOI-induced 5-HT2A receptor-mediated head shakes in rats, Psychopharmacology (Berl), 119(1):9-14 (May 1995).
Crosley, Decreased serotoninergic activity in Tourette syndrome, Ann. Neurol., 5(6):596-7 (Jun. 1979).
Handley et al., Serotonin and Tourette's Syndrome: Movements Such as Head-Shakes and Wet-Dog Shakes May Model Human Tics, pp. 235-253 in: Bradley et al. (eds), Serotonin, CNS Receptors and Brain Function, Proceedings of the Serotonin '91 Conference held in Birmingham, United Kingdom on Jul. 14-17, 1991, Pergamon Press (1992).
Haugbøl et al., Cerebral 5-HT2A receptor binding is increased in patients with Tourette's syndrome, Int. J. Neuropsychopharmacol., 10(2):245-52 (Apr. 2007).
Hayslett et al., Effects of donepezil on DOI-induced head twitch response in mice: implications for Tourette syndrome, Pharmacol. Biochem. Behav., 76(3-4):409-15 (Dec. 2003).
Pringsheim et al., Comprehensive systematic review summary: Treatment of tics in people with Tourette syndrome and chronic tic disorders, Neurology, 92(19):907-915 (May 2019).
Sanberg et al., Nicotine for the treatment of Tourette's syndrome, Pharmacol. Ther., 74(1):21-5 (1997).
Tizabi et al., Nicotine attenuates DOI-induced head-twitch response in mice: implications for Tourette syndrome, Prog. Neuropsychopharmacol. Biol. Psychiatry, 25(7):1445-57 (Oct. 2001).

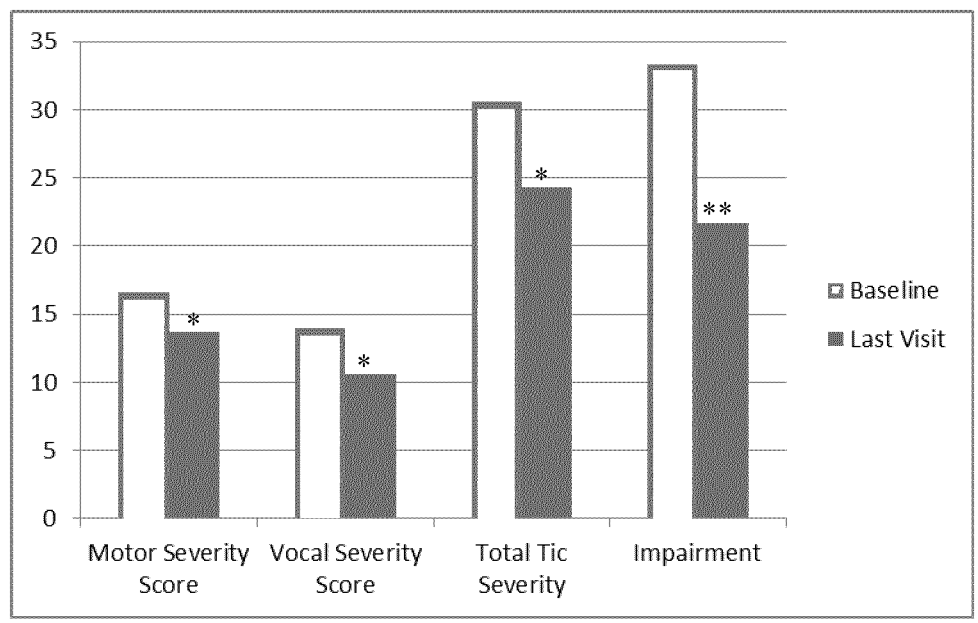
* p<0.001, paired t-test; ** p<0.01

FUSED BENZAZEPINES FOR TREATMENT OF TOURETTE'S SYNDROME

CROSS-REFERENCE TO RELATED APPLICATIONS

This application is a United States National Phase Application of International Application No. PCT/US2013/050337, filed on Jul. 12, 2013, which claims the benefit of the filing date of U.S. Provisional Application No. 61/671,044, which was filed on Jul. 12, 2012. The entire contents of these prior applications are hereby incorporated by reference in their entirety.

FIELD OF THE INVENTION

This invention relates to methods of treating patients suffering from tic disorders, and more particularly to the treatment of Tourette's Syndrome with fused benzazepines.

BACKGROUND

Tourette's syndrome (TS) is a chronic neuropsychiatric disorder characterized by the presence of fluctuating motor and phonic tics. Tics are involuntary or semi-voluntary, sudden, brief, intermittent, repetitive movements (motor) or sounds (phonic) that are classified as simple or complex. Simple tics, for example eye blinking or facial grimacing, are relatively easy to camouflage and may go largely unnoticed. Complex tics, such as body contortions, self-injurious behavior, obscene gestures, or shouting of socially inappropriate word or phrases, can appear to be purposeful actions and are particularly distressing. The typical age of onset is between five and seven years. Affected children may become the target of teasing by peers, which in turn can result in low self-esteem, social isolation, poor school performance, depression and anxiety. In addition to causing social embarrassment, sudden, forceful tics can be painful, and violent head and neck tics have been reported to cause secondary neurologic deficits, such as compressive cervical myelopathy. Tourette's Syndrome patients are also at increased risk for obsessive-compulsive disorder (OCD), depression, and attention-deficit-hyperactivity disorder (ADHD).

Evidence suggests that Tourette's Syndrome is an inherited disorder, although the specific genetic lesion is not known, and there is no cure for tics. Available treatments are not always effective and may be associated with debilitating side effects. There is a continuing need for therapeutic agents for the treatment of Tourette's Syndrome.

Several review articles concerning Tourette's Syndrome are available. These include Felling and Singer, *J. Neurosci.* 31(35):12387-12395, 2011; Cavanna et al., *J. Neuropsychiatry Clin. Neurosci.* 21:13-23, 2009; Kenney et al., *Am. Fam. Physician* 77:651-658, 2008; Muller, *Dialogues Clin. Neurosci.* 9:161-171, 2007; Leckman et al., *Pediatrics* 102:14-19, 1998; and Jankovic, *N. Engl. J. Med.* 345:1184-1192, 2001.

SUMMARY

The present invention encompasses methods of treating a subject who has been diagnosed as having a tic disorder. The methods can include the steps of: (a) identifying a subject in need of treatment; and (b) administering to the subject a therapeutically effective amount of a composition comprising a D1/D5 receptor antagonist, a D1/D5 receptor partial agonist, or a mixture thereof. The subject can be a human and can be of any age (e.g., newborn to about 17, 18, or 21 years old, or a subject who is at least 17, 18, or 21 years old). In some embodiments, the subject is considered to be free from attention-deficit-hyperactivity disorder, depression, and obsessive-compulsive disorder.

The tic disorder can be Tourette's Syndrome, a pediatric autoimmune disorder associated with streptococcal infection (PANDAS), a transient tic disorder, a chronic tic disorder, or a Tic Disorder Not Otherwise Specified (NOS). The subject can exhibit a motor tic (e.g., a complex motor tic), a vocal tic (e.g., a complex vocal tic), or a combination thereof.

The D1/D5 receptor antagonist can be ecopipam or a pharmaceutically acceptable salt, solvate, hydrate, prodrug, structural analog, metabolite, or polymorph thereof. In the course of this application, we may provide lists such as this one. It is to be understood that only one item may be selected; that a combination of items may be selected; and that one or more of the listed items may be excluded. For example, a formulation useful as described herein can include ecopipam; a pharmaceutically acceptable salt of ecopipam; or a mixture of ecopipam and a pharmaceutically acceptable salt thereof. Further, any of these alternatives can explicitly exclude any other listed item. For example, a formulation useful as described herein can include ecopipam but exclude a structural analog thereof.

The compound administered (e.g., a D1/D5 receptor antagonist) can be formulated for oral delivery (e.g., formulated in a unit dosage form of about 0.01 mg/kg to about 500 mg/kg (e.g., about 0.01 mg/kg to about 50 mg/kg; about 0.01 mg/kg to about 5 mg/kg; or about 0.1 mg/kg to about 5 mg/kg)). With respect to daily dosages, the compound administered (e.g., a D1/D5 receptor antagonist) can be administered at a dose of about 50-100 mg/day. The administration can occur once per day or in divided doses, and any of the treatments described herein can include a step of administering a distinct, "second" treatment for treating the tic disorder. For example, the methods of the invention encompass administration of a compound as described herein together with a behavioral therapy, surgical therapy, or distinct pharmaceutical therapy. In one embodiment, the combination therapy is carried out by administering a compound as described herein and a therapeutically effective amount of a second composition for the treatment of attention-deficit-hyperactivity disorder (ADHD), depression, or obsessive-compulsive disorder.

The present invention can be described in terms of "use" and encompasses use of a compound as described herein in the preparation of a medicament for the treatment of a tic disorder. The compound within the medicament can be a D1/D5 receptor antagonist, a D1/D5 receptor partial agonist, or a mixture thereof, and the specific formulation can be as described further herein.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 1 is a bar graph depicting initial results obtained from the clinical trial described below.

DETAILED DESCRIPTION

The present invention is based, in part, on our discovery that compounds that selectively bind the D1/D5 receptor and subsequently inhibit dopamine access to the D1/D5 receptor are effective in treating (by, for example, ameliorating or relieving) one or more symptoms associated with Tourette's Syndrome. Clinical trials are particularly important in this instance because non-human (i.e., animal) models neither effectively replicate the disease nor predict clinical efficacy (see Swerdlow and Sutherland, *Pharmacol. Ther.* 108(3): 281-293, 2005). The clinical study described below is the first demonstration of the activity of D1/D5 antagonists in patients with Tourette's Syndrome.

Accordingly, the methods of the invention encompass the administration of pharmaceutical formulations including selective D1/D5 antagonists to patients suffering from tic disorders, including Tourette's Syndrome. As secondary neurologic deficits result from tic disorders of a certain severity, the present methods can also provide relief from these downstream events. The therapeutic methods described herein can be carried out in connection with other therapies such as behavioral, pharmacologic, and surgical therapies that are designed to reduce the frequency or severity of tics and/or to increase a patient's ability to cope with their symptoms.

fold different. Compounds are also defined as being agonists or antagonists according to their actions at the receptor. With respect to the neurotransmitter dopamine, pure agonists completely mimic the effects of the native neurotransmitter; pure antagonists completely block the actions of an agonist while having no agonist activity of their own; and partial agonists can exhibit mixed actions, showing some degree of intrinsic positive activity at the receptor (albeit less than what would be seen with the native neurotransmitter) while also blocking the actions of an agonist under some conditions.

Compounds useful in the context of the present invention include pure and/or selective D1 receptor antagonists, pure and/or selective D5 antagonists, pure and/or selective D1/D5 receptor antagonists, selective partial antagonists of the D1 receptor, selective partial agonists of the D5 receptor, and selective partial agonists at the D1/D5 receptor. Such compounds can be used alone or in any combination; in some embodiments, the compositions can include a mixture of two or more such compounds in equal or unequal amounts.

The compounds can conform to the generic formula in the table below.

TABLE I

| Col. 1 | Col. 2 | Col. 3 stereo-chemistry | Col. 4 | Col. 5 | Col. 6 Ki (nM) | Col. 7 | Col. 8 |
|---|---|---|---|---|---|---|---|
| Q | n | of 7a and 7b H's | X | Y | $^3$H-23390 | $^3$H-Spip | CAR (MED) |
| $CH_2$ | 1 | cis | $CH_3O$ | OH | 6450 | >100,000 | |
| $CH_2$ | 1 | cis | HO | $CH_3O$ | 44,800 | >100,000 | |
| $CH_2$ | 1 | trans | $CH_3O$ | OH | 23 | 2500 | 30 (po); 0.3-1 (sc) |
| $CH_2$ | 1 | trans | HO | $CH_3O$ | 2970 | >100,000 | |
| $CH_2$ | 1 | trans | Cl | OH | 5.5 | 11,500 | 30 (po); 0.3 (sc) |
| $CH_2$ | 1 | 7b(S):7a(R)(+) | Cl | OH | 1800 | >100,000 | >30 (po) |
| $CH_2$ | 1 | 7b(R):7a(S)(−) | Cl | OH | 12 | 14,300 | 30 (po) |
| $CH_2$ | 1 | cis | Cl | OH | 6200 | >100,000 | |
| $CH_2$ | 1 | trans | H | OH | 80 | 3500 | |
| $CH_2$ | 2 | trans | $CH_3O$ | OH | 292 | >100,000 | 10 (sc) |
| $CH_2$ | 2 | trans | HO | $CH_3O$ | 7730 | >100,000 | 10 (sc) |
| $CH_2$ | 1 | trans | $CH_3$ | OH | 119 | 7200 | |
| $CH_2$ | 1 | trans | Cl | $NH_2$ | 70 | 4175 | 3 (po) |
| O | 1 | trans | H | OH | 121 | — | |
| $CH_2$ | 0 | trans | Cl | OH | 10 | 2600 | |

Compositions suitable for use in the present methods include compounds that selectively bind to the D1 and/or the D5 receptor and pharmaceutical compositions containing such compounds. As is known in the art, dopamine is a neurotransmitter active within the central nervous system, and its receptors have been classified into two families based on their genetic structure: the D1 family including the subtypes D1 and D5, and the D2-family including the subtypes D2, D3, and D4 (see, e.g., Civelli et al., *Ann. Rev. Pharmacol. Toxicol.* 32:281-307, 1993; and Emillien et al., *Pharmacol. Therap.* 84:133-156, 1999).

Although there are no universally accepted criteria, compounds are typically said to be selective for one receptor over another when their binding affinities are at least 100-

Such compounds are known in the art and are more fully described in U.S. Pat. No. 4,973,586, which is hereby incorporated by reference in its entirety.

In one embodiment, the compound can be a metabolite of ecopipam or another compound described herein. For example, the compound can be a desmethyl compound, such as the desmethyl form of ecopipam, which has been referenced in the art as SCH 40853.

More specifically, the compound can be:

1) 6,7,7a,8,9,13b-hexahydro-2-hydroxy-3-methoxy-7-methyl-5H-benzo[d]naphtho[2,1-b]azepine;

2) 6,7,7a,8,9,13b-hexahydro-2-hydroxy-7-methyl-5H-benzo[d]naphtho[2,1-b]azepine;

3) 6,7,7a,8,9,13b-hexahydro-3-chloro-2-hydroxy-7-methyl-5H-benzo[d]naphtho[2,1-b]azepine;
4) 6,7,7a,8,9,13b-hexahydro-2-hydroxy-3,7-dimethyl-5H-benzo[d]naphtho[2,1-b]azepine;
5) 6,7,7a,8,9,13b-hexahydro-2-amino-7-methyl-5H-benzo[d]naphtho[2,1-b]azepine;
6) 6,7,7a,8,9,13b-hexahydro-2-amino-3-chloro-7-methyl-5H-benzo[d]naphtho[2,1-b]azepine;
7) 6,7,7a,8,9,13b-hexahydro-2-amino-3,7-dimethyl-5H-benzo[d]naphtho[2,1-b]azepine;
8) 6,6a,7,8,9,13b-hexahydro-12-methoxy-7-methyl[1]benzopyrano[4,3-a][3]benzazepine;
9) 6,6a,7,8,9,13b-hexahydro-7-methyl[1]benzopyrano[4,3-a][3]benzazepin-12-ol;
10) 6,6a,7,8,9,13b-hexahydro-3-hydroxy-2-methoxy-7-methyl-5H-benzo[d]naphtho[2,1-b]azepine;
11) 2-hydroxy-3-methoxy-7-methyl-5,6,7,7a,8,9,10,14b-octahydro-benzo[d]benzo[3,4]cyclo-hepta[1,2-b]azepine;
12) 3-hydroxy-2-methoxy-7-methyl-5,6,7,7a,8,9,10,14b-octahydro-benzo[d]benzo[3,4]cyclo-hepta[1,2-b]azepine;
13) 5,6,7,7a,8,12b-hexahydro-2-hydroxy-3-chloro-7-methyl-benz[d]indeno[2,1-b]azepine;
14) 5,6,7,7a,8,12b-hexahydro-2-hydroxy-3-methoxy-7-methyl-benz[d]indeno[2,1-b]azepine;
15) 5,6,7,7a,8,12b-hexahydro-2-amino-3-chloro-7-methyl-benz[d]indeno[2,1-b]azepine;
16) 5,6,7,7a,8,12b-hexahydro-2-hydroxy-7-methyl-benz[d]indeno[2,1-b]azepine;
17) 5,6,7,7a,8,12b-hexahydro-3,7-dimethyl-2-hydroxy-benz[d]indeno[2,1-b]azepine;
18) 5,6,7,7a,8,12b-hexahydro-3-chloro-7-cyclopropylmethyl-2-hydroxy-benz[d]indeno[2,1b]azepine;
19) 5,6,7,7a,8,12b-hexahydro-7-allyl-3-chloro-2-hydroxy-benz[d]indeno[2,1-b]azepine;
20) 5,6,7,7a,8,12b-hexahydro-3-chloro-2-hydroxy-7,8,8-trimethyl-benz[d]indeno[2,1-b]azepine;
21) 5,6,7,7a,8,11b-hexahydro-3-chloro-7-methylthieno[2',3':4,5]cyclopenta[1,2-a][3]benzazepine-2-ol;
22) 5,6,7,7a,8,12b-hexahydro-2-hydroxy-3-chloro-benz[d]indeno[2,1-b]azepine;
23) 6,7,7a,8,9,13b-hexahydro-3-chloro-2-hydroxy-5H-benzo[d]naphtho[2,1-b]azepine; or
24) 6,7,7a,8,9,13b-hexahydro-2-amino-3-trifluoromethyl-7-methyl-5H-benzo[d]naphtho[2,1b]azepine.

As noted elsewhere herein the compound administered can be in the form of a pharmaceutically acceptable salt and/or a trans isomer. An exemplary D1/D5 receptor antagonist useful in the methods of the invention is SCH39166, which is also known as PSYRX101 or ecopipam (6,7,7a,8,9,13b-hexahydro-3-chloro-2-hydroxy-5H-benzo[d]naphtho[2,1-b]azepine or, in trans form, (−)-trans-6,7,7a,8,9,13b-hexahydro-3-chloro-2-hydroxy-5H-benzo[d]naphtho[2,1-b]azepine). Ecopipam conforms to the structure:

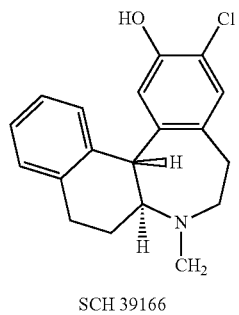

SCH 39166

In vitro binding studies using rat brain homogenates show that ecopipam has high affinity for D1/D5 receptors at low concentrations (see Chipkin et al., *J. Pharmacol. Exp. Ther.* 247:1092-1102, 1988; and McQuade et al., *J. Neurochem.* 57:2001-2010, 1991). Additional binding studies versus D2-selective ligands ($^3$H-spiperone) showed that ecopipam was roughly 1000-fold selective for the D1 vs. the D2 receptor, and 100-fold selective versus the serotonin receptor (versus $^3$H-ketanserin). Moreover, it did not bind at concentrations >700-fold to any of the following sites: adenosine, benzodiazepine, glutamate/AMPA/kainate, GABA, muscarinic, nicotinic, opiate, or alpha- or beta-adrenergic sites.

Activation of D1 receptors by dopamine and similar agonists stimulates the production of cyclic AMP (cAMP) via activation of adenylate cyclase. In vitro studies on this neuronal second messenger confirmed that ecopipam was an antagonist. In vivo studies on dopamine-agonist-induced behaviors (e.g., selective D1-agonist discriminative stimulus conditions in rats) likewise showed that ecopipam was a selective D1 antagonist in animals (Haile et al., *Eur. J. Pharmacol.* 38:125-131, 2000). To ensure that there was no species specificity to the receptor binding profile, ecopipam's potency and selectivity were evaluated using cloned human receptors. Ecopipam bound with high affinity to hD1/hD5 receptors, but was >700-fold selective versus the hD2, hD3, and hD4 receptors. Positron emission tomography (PET) studies using radiolabeled ecopipam have been conducted in healthy volunteers (Karlsson et al., *Psychopharmacol.* 121:300-308, 1995). The results showed specific binding in the human brain, and that binding corresponded to the known distribution of dopamine D1 receptors.

Other exemplary D1/D5 receptor antagonists that are useful in the present methods include: SCH23390 and compounds related thereto, including SCH 12679 and the compounds described in U.S. Pat. No. 4,477,378 (which is hereby incorporated by reference in the present application in its entirety), BTS-73-947, NNC-22-0010, JHS-271, JHS-198, JHS-136, A69024, and NNC687. Exemplary D1/D5 partial agonists include SKF38393, fenoldapam; SKF75670A; SKF 81297; SKF82958; and dinapsoline.

The structures of some of these compounds are illustrated here:

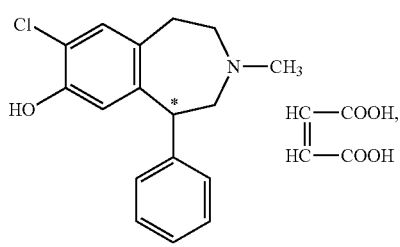

SCH 23390

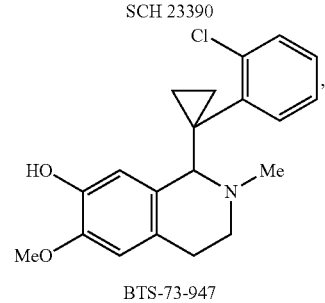

BTS-73-947

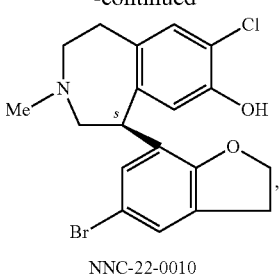

NNC-22-0010

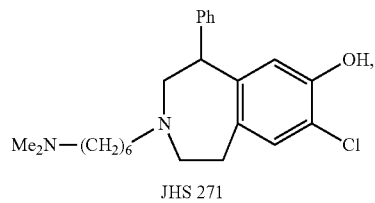

JHS 271

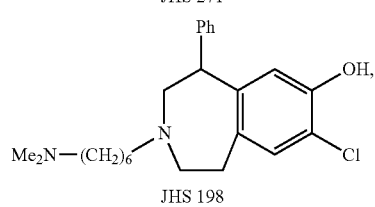

JHS 198

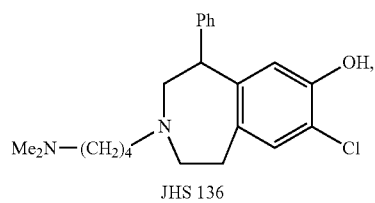

JHS 136

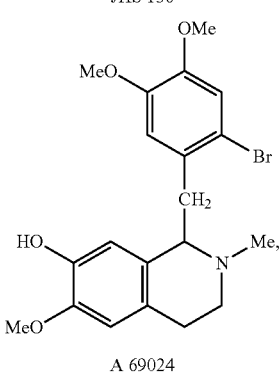

A 69024

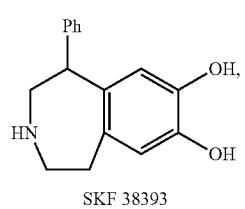

SKF 38393

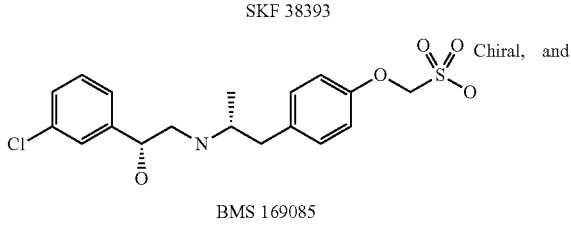

BMS 169085

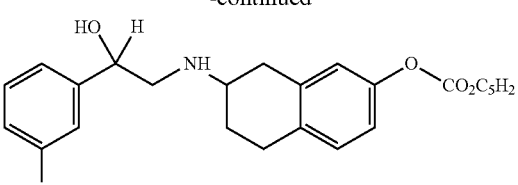

SR 58611A

The chemical names of these compounds appear in the following Table:

| | |
|---|---|
| SCH 39166 (ecopipam) | (−)-trans-6,7,7a,8,9,13b-hexahydro-3-chloro-2-hydroxy-N-methyl-5H-benzo [d]-naphtho-[2,1-b]azepine |
| SCH 23390 | (d)-7-chloro-8-hydroxy-3-methyl-1-phenyl-2,3,4,5-tetrahydro-1H-3-benzazepine maleate |
| BTS-73-947 | 1-[1-(2-chlorophenyl)cyclopropyl]-1,2,3,4-tetra-hydro-7-hydroxy-6-methoxy-2-methyl-(S)-isoquinolinol |
| NNC-22-0010 | (+)-5-(5-bromo-2,3-dihydro-7-benzofuranyl)-8-chloro-2,3,4,5-tetrahydro-3-m ethyl-1H-3-benzazepin-7-ol |
| JHS-271 | 8-chloro-3-[6-(dimethylamino)hexyl]-2,3,4,5-tetra-hydro-5-phenyl-1H-3-benzazepin-7-ol |
| JHS-198 | 8-chloro-3-[6-(dimethylamino)hexyl]2,3,4,5-tetra-hydro-5-phenyl-1H-3-benzazepin-7-ol with boranecar-bonitrile (1:1). |
| JHS-136 | 8-chloro-3-[4-(dimethylamino)butyl]-2,3,4,5-tetra-hydro-5-phenyl-1H-3-benzazepin-7-ol |
| A-69024 | 1-[(2-bromo-4,5-dimethoxyphenyl)methyl]-1,2,3,4-tetra-hydro-6-methoxy-2-met hyl-7-isoquinolinol |

Compounds useful in the present invention can be prepared in a variety of ways known to one of ordinary skill in the art of organic synthesis. Starting materials are readily available, and it will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by one of ordinary skill in the art by routine optimization procedures. Thus, the foregoing D1/D5 antagonists can be prepared by known methods. For example, one of ordinary skill in the art could synthesize compounds by the methods described in U.S. Pat. No. 5,302,716, which is hereby incorporated by reference in its entirety, and such compounds are useful in the present methods. One could also consult the published PCT applications WO 93/13073; WO 93/1702; WO 95/25102. One could also consult J. Med. Chem. 38(21):4284-4293 (1995). An exemplary D1/D5 partial agonist is SKF 38393, having the chemical name 2,3,4,5-tetrahydro-1-phenyl-1-H-3-benzazepine-7,8-diol. Other compounds useful in the present invention are those described in U.S. Pat. No. 4,477,378 (esters of substituted 8-hydroxy-1-phenyl-2,3,4,5-tetra-hydro-1H-3-benzazepines), which is hereby incorporated by reference herein in its entirety.

Ecopipam free base is a benzazepine derivative that is a selective antagonist of the D1 family of receptors. Ecopipam hydrochloride (SCH 39166 HCl; $C_{19}H_{20}NOCl \cdot HCl$) has the chemical structure:

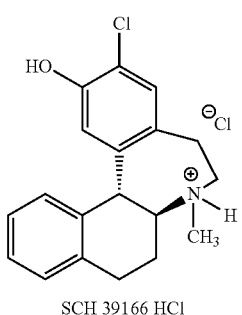

SCH 39166 HCl

The compounds described herein, including those conforming to any formula, can be asymmetric (e.g., having one or more stereocenters). All stereoisomers, such as enantiomers and diastereomers, are intended unless otherwise indicated. The present compounds that contain asymmetrically substituted carbon atoms can be used in mixed form or isolated in optically active or racemic forms. A compound useful in the methods of the invention can have a trans configuration. Methods for preparing optically active forms from optically active starting materials are known in the art. These methods include resolution of racemic mixtures and stereoselective synthesis. For example, one can carry out fractional recrystallization using a chiral resolving acid that is an optically active, salt-forming organic acid. Suitable resolving agents for use in these methods can be, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other useful resolving agents include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like. Resolution of racemic mixtures can also be carried out by elution on a column packed with an optically active resolving agent (e.g., dinitrobenzoylphenylglycine). Suitable elution solvent composition can be determined by one skilled in the art.

Cis and trans geometric isomers of the present compounds are described and may be isolated as a mixture of isomers or as separated isomeric forms. Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Tautomeric forms can be in equilibrium or sterically locked into one form by appropriate substitution.

Compounds of the invention also include all isotopes of atoms occurring in the intermediate or final compounds. Isotopes include those atoms having the same atomic number but different mass numbers. For example, isotopes of hydrogen include tritium and deuterium.

The term "compound," as used herein with respect to any compound conforming to one of the D1/D5 antagonists or partial agonists described above, is meant to include all stereoisomers, geometric iosomers, tautomers, and isotopes of the structures referenced (e.g., depicted). All compounds, and all pharmaceutically acceptable salts thereof, can be used in a solvated or hydrated form. In some embodiments, the compounds of the invention (regardless of form; e.g., salts) are "substantially isolated," meaning that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99%, by weight, of a compound of the invention. Methods for isolating compounds and their salts are routine in the art.

As noted, the present methods can be carried out using "pharmaceutically acceptable salts," a term that generally refers to derivatives of the disclosed compounds wherein the parent compound is modified by converting an existing acid or base moiety to its salt form. "Pharmaceutically acceptable" generally encompasses those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit:risk ratio. Examples of pharmaceutically acceptable salts include, but are not limited to, mineral or organic acid salts of basic residues such as amines; alkali or organic salts of acidic residues such as carboxylic acids; and the like. The pharmaceutically acceptable salts useful in the methods of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile (ACN) are preferred. Lists of suitable salts are found in Remington's Pharmaceutical Sciences, 17th ed., Mack Publishing Company, Easton, Pa., 1985, p. 1418 and the *Journal of Pharmaceutical Science*, 66:2, 1977.

In addition to, or instead of, ecopipam hydrochloride, ecopipam free base may be in the form of another pharmaceutically acceptable salt. Such salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluensulfonic, methanesulfonic, ethane dislfonic, oxalic, isethionic, and the like.

The compounds and compositions disclosed herein are generally and variously useful for treatment of tic disorders, including Tourette's Syndrome, which is also variously referred to as Tourette Syndrome, Tourette's Disorder, Gilles de la Tourette syndrome (GTS), or simply Tourette's or TS. The tic disorder may also be a pediatric autoimmune disorder associated with streptococcal infection (PANDAS), a transient tic disorder, a chronic tic disorder, or a Tic Disorder Not Otherwise Specified (NOS). Transient tic disorders are generally characterized by multiple motor and/or phonic tics that occur for at least four weeks but less than 12 months. Chronic tic disorders are generally characterized by either single or multiple motor or phonic tics, but not both, which are present for more than a year; Tourette's Syndrome is diagnosed when both motor and phonic tics are present (although not necessarily concurrently) for more than one year. Tic Disorder NOS is diagnosed when tics are present but do not meet the criteria for any specific tic disorder. The present compounds and compositions can also be administered for the treatment of tics induced as a side effect of a medication; tics associated with autism; and Tourettism (the presence of Tourette-like symptoms in the absence of Tourette's Syndrome (e.g., as a result of another disease or condition, such as a sporadic, genetic, or neurodegenerative disorder)).

The compounds and compositions disclosed herein are also useful for the treatment of movement disorders more generally. These disorders include akinetic-rigid syndrome, chorea (e.g., as occurs in Huntington's Disease), myoclonus and/or dystonia of any etiology, tremor, or Parkinson's Disease. The movement disorder may also be one induced by a medication or other stimulus to which a patient has been exposed. For example, the compounds and compositions disclosed herein can be used to alleviate dyskinesias induced by dopamine agonists (e.g., including but not limited to levodopa, levodopa and carbidopa combinations, ropinirole, pramipexole, or pergolide) and tardive dyskinesias induced by anti-psychotic drugs (e.g., including but not limited to haloperidol, risperidone, olanzapine, quetiapine, aripiprazole, ziprasidone, paliperidone, iloperiodone, perphenazine, metoclopramide, and chlorpromazine).

The compounds and compositions described herein can be administered to a subject, which we may also refer to as a "patient." While human patients are clearly intended to be treated, the invention is not so limited. As the compositions are likely to be relatively inexpensive to manufacture, the invention encompasses methods of veterinary use (e.g., the treatment of house pets such as cats and dogs). Subjects are effectively treated whenever a clinically beneficial result ensues. This may mean, for example, a complete or marked resolution of the symptoms of a disorder, a decrease in the frequency, severity, and/or duration of the symptoms, or a slowing of the disorder's progression. Thus, an effective treatment for tic disorders could manifest as a decrease in the number, duration, frequency and/or intensity of either motor tics, phonic tics, or both motor and phonic tics. Preferably, there is no significant toxicity in the patient. The level of toxicity, if any, can be determined by assessing a patient's clinical symptoms before and after administering a known amount of a particular composition.

Any of the methods described herein can include a step of identifying a subject (e.g., a patient and, more specifically, a human patient) who has a tic disorder. Following diagnosis or in conjunction with diagnostic tests, the methods can then include the step of providing to the subject a compound or composition described herein. "Providing" the compound or composition encompasses a direct administration (e.g., a person practicing the method can directly administer the compound or composition to the patient) as well as indirect administration (e.g., a person practicing the method can give the patient a composition which they then self-administer; a person practicing the method can give the patient a prescription for a composition, which the patient then fills and self-administers). A "therapeutically effective amount" of a composition is an amount that results in marked resolution of the patient's symptoms; a decrease in the frequency, severity, or duration of their symptoms; or a slowing of the disorder's progression. Any of the present methods may also include a step of monitoring the patient (by physical examination and/or interview) to help optimize dosing and scheduling as well as to help predict and optimize outcome.

As noted, the methods described herein are useful for the treatment of tics. Tics can take many forms, but typically consist of simple, repetitive or sequential movements, gestures, and utterances that mimic fragments of normal behavior. Simple motor tics involve only a single muscle or a group of muscles, and often cause a brief, jerking movement (clonic tics); they may also be slower, causing a briefly sustained abnormal posture (dystonic tics) or an isometric contraction (tonic tics). Examples of simple clonic motor tics include blinking, nose twitching, and head and limb jerking Dystonic tics include sustained eye closure (blepharospasm), ocular deviations, bruxism, mouth opening, torticollis, sustained jaw opening, and shoulder rotation. Tonic tics are typically manifested by abdominal contraction, limb extension or limb flexion. Examples of complex motor tics include head shaking, trunk bending or gyrating, brushing hair, touching, throwing, hitting, jumping, kicking, making rude gestures, burping, vomiting, retching, smelling objects, grabbing one's genitalia and making other lewd or obscene gestures (copropraxia), and imitating others' gestures (echopraxia).

Simple phonic tics typically include sniffing, throat clearing, grunting, squeaking, screaming, coughing, barking, blowing, throat clearing, and making sucking sounds. Complex phonic tics include linguistically meaningful utterances and verbalizations, such as the shouting of obscenities, profanities, or otherwise socially inappropriate words or phrases (coprolalia), the repetition of someone else's words or phrases (echolalia), and the repetition of one's own utterances, particularly the last syllable, word, or phrase in a sentence (palilalia).

The methods disclosed herein can be applied to both pediatric and adult subjects.

Regardless of their original source or the manner in which they are obtained, the compounds of the invention can be formulated in accordance with their use. For example, the compounds can be formulated within compositions for administration to a patient (i.e., formulated as pharmaceutical compositions). These compositions can be prepared according to methods well known in the pharmaceutical art and can be administered by a variety of routes. Administration may be topical (including ophthalmic or ocular (e.g., via eye drops) and to mucous membranes (i.e., transmucosal) including buccal, intranasal, vaginal and rectal delivery), pulmonary (e.g., by inhalation or insufflation of powders or aerosols, including by nebulizer), intranasal, epidermal (and transdermal), ocular, or oral. While oral administration is preferable for its convenience, parenteral formulations can also be used, and such formulations can be administered intravenously, intraarterially, subcutaneously, intraperitoneally or intramuscularly (e.g., by injection or infusion). As dopaminergic receptors within the brain are targeted, intracranial (e.g., intrathecal or intraventricular) administration is also contemplated and within the scope of the present methods. Parenteral administration can be in the form of a single bolus dose, or may be, for example, by a continuous perfusion pump. Thus, the formulations include depot formulations, including those that allow for slow-release. For administration by a variety of routes, the compounds described herein can be associated with nano- or microparticles. Pharmaceutical compositions and formulations for topical administration may include transdermal patches, ointments, lotions, creams, gels, drops, suppositories, sprays, liquids, powders, and the like. Conventional pharmaceutical carriers, aqueous, powder or oily bases, thickeners and the like may be necessary or desirable.

Pharmaceutical compositions useful in the present methods can include an active ingredient (one or more of the compounds described herein) in combination with one or more pharmaceutically acceptable carriers. In making pharmaceutical compositions, the active ingredient is typically mixed with an excipient, diluted by an excipient or enclosed within such a carrier in the form of, for example, a capsule, tablet, sachet, paper, or other container. When the excipient serves as a diluent, it can be a solid, semisolid, or liquid material (e.g., normal saline or a buffered saline such as phosphate-buffered saline) that acts as a vehicle, carrier, or medium for the active ingredient. Thus, the compositions can be in the form of capsules (e.g., soft or hard gelatin capsules), tablets, pills, powders (e.g., sterile packaged powders), lozenges, sachets, cachets, elixirs, suspensions, emulsions, solutions (e.g., sterile injectable solutions), suppositories, syrups, aerosols (as a solid or in a liquid medium), or ointments. These forms can contain, for example, up to about 10% by weight of the active compound. In other embodiments, these forms can contain at least or more than 10% by weight of the active compound (e.g., at least or about 15%, 20%, 25%, 35% or 50% by weight of the active compound). As is known in the art, the type of diluent can vary depending upon the intended route of administration. The resulting compositions can include additional agents, such as coloring, flavoring, or a preservative. The compounds may also be applied to or contained within a drug delivery device such as a pump or patch. The compounds of the invention can be administered alone or in a mixture in the presence of a pharmaceutically acceptable excipient that is selected on the basis of the mode and route of administration. Suitable pharmaceutical excipients as well as pharmaceutical necessities for use in pharmaceutical formulations are described in Remington's Pharmaceutical Sciences (E. W. Martin), a well-known reference text in this field, and in the USP/NF (United States Pharmacopeia and the National Formulary). Other sources are also available to one of ordinary skill in the art. In preparing a formulation, the active compound can be milled to provide the appropriate particle size prior to combining with the other ingredients. If the active compound is substantially water insoluble, it can be milled to a particle size of less than 200 mesh to improve dissolution. If the active compound is substantially water soluble, the particle size can be adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, and other cellulose derivatives. The formulations can additionally include one or more of: a lubricating agent such as talc, magnesium stearate, and mineral oil; a wetting agent; an emulsifying and suspending agent; a preserving agent such as methyl- and propylhydroxy-benzoates; a sweetening agent; and a flavoring agent. The pharmaceutical compositions can be formulated so as to provide quick, sustained, or delayed release of the active ingredient after administration to the patient by employing procedures known in the art.

The compositions can be formulated in a unit dosage form, each dosage containing, for example, from about 0.1 mg to about 500 mg. For example, the present compounds can be formulated with a unit dosage form of about 0.1 mg to about 50 mg, from about 0.1 mg to about 40 mg, from about 0.1 mg to about 20 mg, from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg, from about 0.5 mg to about 20 mg, from about 0.5 mg to about 10 mg, from about 0.5 mg to about 5 mg; from about 1 mg from to about 50 mg, from about 1 mg to about 30 mg, from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 250 mg to about 500 mg, from about 300 mg to about 450 mg, from about 300 mg to about 400 mg, or from about 50 mg to about 100 mg of the active ingredient.

The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 500 mg of the active ingredient of the present invention.

Oral formulations (e.g., tablets, pills, or capsules) can be coated or otherwise compounded to provide a dosage form affording the advantage of prolonged action. For example, the oral formulation can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. Other examples of modified release dosage forms include matrix tablets, with or without additional coating; granules or beads in a capsule, the granules or beads being formulated with or without release modifying excipients or coatings; coated capsules; osmotic pumps, with or without additional coatings; and so on. A variety of materials can be used for such enteric layers or coatings, including a number of polymeric acids and mixtures of polymeric acids with materials such as shellac, cetyl alcohol, and cellulose acetate.

Liquid forms in which the compounds can be incorporated for administration orally or by injection include aqueous solutions, suitably flavored or unflavored syrups, aqueous or oil suspensions, and flavored emulsions with edible oils such as cottonseed oil, sesame oil, soybean oil, coconut oil, or peanut oil, as well as elixirs and similar pharmaceutical vehicles. Oral suspensions can also be formulated in non-aqueous water-miscible vehicles such as propylene glycol or glycerin. Compositions for inhalation or insufflation include solutions and suspensions in pharmaceutically acceptable, aqueous or organic solvents, or mixtures thereof, and powders. In some embodiments, the compositions are administered by the oral or nasal respiratory route for systemic effect. The compositions can be nebulized by use of inert gases and then breathed directly from a nebulizing device. In more extreme situations, the nebulizing device can be attached to a face mask, tent, or intermittent positive pressure breathing machine. Oral and nasal delivery formulations can include solution, suspension, or powdered compositions.

Any of the compositions can be sterilized by conventional sterilization techniques or may be sterile filtered. Aqueous solutions can be packaged for use as is or lyophilized. The lyophilized preparation can then be combined with a sterile aqueous carrier prior to administration. The pH of the compound preparations typically will be between about 3 and 11 (e.g., between about 5 to 9; between about 6 to 7; or between about 7 to 8). It will be understood that use of certain of the foregoing excipients, carriers, or stabilizers could result in the formation of pharmaceutical salts.

The proportion or concentration of the compounds of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. By "about" we mean within 10%, plus or minus, of the specified value.

The therapeutic dosage of the compounds of the present invention can vary according to, for example, the particular use for which the treatment is made, the nature of the formulation, the manner and/or route of administration of the compound, the health and condition of the patient (including, for example, size, weight, surface area, age, and sex, and other drugs being administered), and the judgment of the attending clinician. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. In some embodiments, the dose can be, for example, about 1 mg/kg, 2 mg/kg, 5 mg/kg, 10 mg/kg, 20 mg/kg, 50 mg/kg or 100 mg/kg. The dosage is likely to depend on such variables as the type and extent of progression of the disease or disorder, the overall health status of the particular patient, the relative biological efficacy of the compound selected, formulation of the excipient, and its route of administration. Variations in these dosage levels can be adjusted using standard empirical routines for optimization, as is well understood in the art. Administrations can be single or multiple (e.g., a dosage for one patient can be 2- to 3-, or 4-, 6-, 8-, 10-, 20-, 50-, 100-, 150-, or more fold than the dosage for another patient). Encapsulation of the compounds in a suitable delivery vehicle (e.g., polymeric nano- or microparticles or implantable devices) may increase the efficiency of delivery.

The frequency of administration can vary and includes single or multiple doses per day. The compositions can also be taken as needed ("PRN dosing"). The duration of treatment with any composition provided herein can be any length of time from as short as one day to as long as the life span of the host (e.g., many years). For example, a compound can be administered once a day, once a week (for, for example, 4 weeks to many months or years); once a month (for, for example, three to twelve months or for many years); or once a year for a period of five years, ten years, or longer. It is also noted that the frequency of treatment can be variable. For example, the present compounds can be administered once (or twice, three times, etc.) daily, weekly, monthly, or yearly.

The compositions may also be administered along with other treatments, including nonpharmacologic therapies, pharmacologic therapies and surgical treatments. Exemplary nonpharmacologic therapies include reassurance and environmental modifications, identification and avoidance of triggers, and cognitive behavior therapy. Pharmacologic therapies include α2-adrenergic agonists, e.g., including but not limited to clonidine and guanfacine; dopamine receptor-blocking drugs, e.g., including but not limited to haloperidol, pimozide, fluphenazine, olanzapine, risperidone; dopamine-depleting drugs, e.g., including but not limited to tetrabenazine; anti-epileptics, e.g., including but not limited to topiramate; and botulinum toxin injections. Surgical treatments, e.g., deep brain stimulation, may also be used. Concurrent administration of two or more therapeutic agents does not require that the agents be administered at the same time or by the same route, as long as there is an overlap in the time period during which the agents are exerting their therapeutic effect. Simultaneous or sequential administration is contemplated, as is administration on different days or weeks.

Compositions for treating Tourette's Syndrome may also be administered along with (i.e., in addition to) a treatment for a comorbid condition such as ADHD, depression, an eating or sleeping disorder, or OCD, if these conditions are present in a given patient. Therapeutic agents useful for ADHD include but are not limited to stimulants such as methylphenidate and non-stimulants such as atomoxetine. Therapeutic agents useful for depression and OCD include but are not limited to selective serotonin reuptake inhibitors (SSRIs), mixed SSRIs (e.g., venlafaxine), monoamine oxidase inhibitors, and atypical anti-depressants such as dopamine-reuptake inhibitors (e.g., buprorion). Therapeutic agents useful for sleeping disorders include all barbiturates, all benzodiazepines, and other non-benzodiazepine-sedative-hypnotics (e.g., zolpidem, eszopiclone, zoplicone), and all sedating anti-histamines.

The compounds and compositions described herein can be packaged in suitable containers together with information and instructions for use (e.g., a label, other printed material), or information convey by other media (e.g., audio or visual media) as a therapy to treat a tic disorder. Accordingly, packaged products (e.g., sterile containers containing one or more of the compounds described herein and packaged for storage, shipment, or sale at concentrated or ready-to-use concentrations) and kits, including at least one compound of the invention and instructions for use as described herein, are also within the scope of the invention. A product can include a container (e.g., a vial, jar, bottle, bag, or the like) containing one or more compounds of the invention. In addition, an article of manufacture further may include, for example, packaging materials, instructions for use, syringes, buffers or other control reagents for treating or monitoring the condition for which prophylaxis or treatment is required. Instructions for use can be associated with the container (e.g., affixed to the container) and can describe the manner in which the compound therein should be administered (e.g., the frequency and route of administration), indications therefor, and other uses. The compounds can be ready for administration (e.g., present in dose-appropriate units), and may include a pharmaceutically acceptable adjuvant, carrier or other diluent and/or an additional therapeutic agent as described above. Alternatively, the compounds can be provided in a concentrated form with a diluent and instructions for dilution.

For clarity and to obviate an excessively long specification, certain features of the invention are described in the context of separate embodiments. The inventors intend, and one of ordinary skill in the art will appreciate, that a feature described in the context of one embodiment can be included in another embodiment, in addition to or in place of, the particular feature(s) described there. In other words, features described in separate embodiments can also be used in combination in a single embodiment that is distinct from those specifically set out herein. Thus, various features of the invention that are described in the context of a single embodiment, for the purpose of reasonable brevity, can also be provided separately or in any suitable sub-combination.

EXAMPLES

Example 1

A clinical program was carried out to test the safety, tolerability, and activity of ecopipam in adult patients with Tourette's Syndrome. A multicenter, open-label, nonrandomized study in 25 to 30 subjects was conducted to assess the activity and safety of ecopipam in subjects with TS. Eligible subjects were started on an 8-week treatment period with ecopipam and were seen in the clinic every other week (with telephone contacts on the alternate weeks). Assessment was performed at each visit. A follow-up visit was conducted via telephone at Week 10 to record any adverse events. Ecopipam was administered daily before bedtime at 50 mg/day for Week 1 and Week 2 and at 100 mg/day for Weeks 3-8. This treatment regimen is within the scope of the present invention; the compositions and various formulations described herein can be administered as described in this Example.

The activity of ecopipam was measured using the following clinical rating scales: (1) Yale Global Tic Severity Scale (YGTSS; data based on this scoring system are presented below); (2) ADHD self-report symptom checklist (ASRS); (3)Yale-Brown Obsessive Compulsive Scale (YBOCS); (4) Premonitory Urge for Tics Scale (PUTS-1); (5) HAM-D; and (6) Clinical Global Impression Improvement and Severity Scales (CGI).

The demographics of the study population were as follows: eighty three percent of the subjects were male (15 out of 18); fifteen were Caucasian, two were African-American, and one was an Asian/Pacific Islander. All subjects reported at least one adverse event (AE). There were no serious adverse events (i.e., requiring medical intervention; AEs). Four patients reported AEs that were rated as severe and included the following: sedation, insomnia, decreased appetite, hypersensitivity, cold sweat, and feeling jittery. The following AEs were rated mild to moderate and were reported in more than three subjects: fatigue, insomnia, nausea, sedation, headache, restlessness, anxiety, muscle twitching, dysphoria, and sleeplessness. These side effects are similar to those seen in other studies with ecopipam and were not unexpected.

Sporadic changes in lab tests were observed, but none were of clinical significance. Likewise, there were no clinically significant changes in vital signs.

The changes in YGTSS scores between a baseline assessment and assessment at the patient's last visit are summarized in FIG. 1 for the fifteen patients who completed the trial. In these patients, ecopipam produced a highly statistically significant (Paired t-Test p<0.001) reduction in YGTSS scores (motor, phonic, and total severity scores). An intent to treat analysis of the entire population (n=18) showed that the statistically significant changes were evident even when the data from all eighteen patients were included.

The improvement in the YGTSS scores were consistent with the significant changes in the Clinical Global Severity (CGI-S) scores where 9 of the 15 patients (60%) showed at least one grade change in their scores (p≤0.01 Student's t test).

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating Tourette's disorder in a human patient in need thereof, the method comprising:
   administering to the patient 0.01 mg/kg to 500 mg/kg per day of ecopipam or a pharmaceutically acceptable salt thereof.

2. The method of claim 1, wherein the patient is not older than 18 years.

3. The method of claim 1, wherein the patient is considered to be free from attention-deficit-hyperactivity disorder, depression, and obsessive-compulsive disorder.

4. A method of treating Tourette's Disorder in a human patient in need thereof, the method comprising
   administering to the patient about 0.1 mg to about 500 mg per day of ecopipam or a pharmaceutically acceptable salt thereof.

5. The method of claim 4, comprising administering ecopipam hydrochloride.

6. The method of claim 5, wherein the ecopipam is formulated for oral delivery.

7. The method of claim 6, wherein the ecopipam is administered at a daily dose in a range of about 0.01 mg/kg to about 50 mg/kg.

8. The method of claim 7, wherein ecopipam is administered at a daily dose in a range of about 0.1 mg/kg to about 5 mg/kg.

9. The method of claim 7, wherein the ecopipam is administered at a dose of 50-100 mg/day.

10. The method of claim 4, wherein the ecopipam is administered once, twice, or three times daily.

11. The method of claim 1, further comprising a step of administering a second treatment for treating the tic disorder.

12. The method of claim 11, wherein the second treatment is a behavioral, surgical, or pharmaceutical therapy.

13. The method of claim 1, further comprising a step of administering to the subject a therapeutically effective amount of a second composition for the treatment of attention-deficit-hyperactivity disorder, depression, or obsessive-compulsive disorder.

14. The method of claim 1, wherein the composition is formulated in a unit dosage form.

15. The method of claim 1, wherein the composition is formulated as a capsule, tablet, pill, powder, or syrup.

16. The method of claim 1, comprising administering 0.01 mg/kg to 50 mg/kg per day of ecopipam or a pharmaceutically acceptable salt thereof.

17. The method of claim 16, comprising administering ecopipam hydrochloride.

18. The method of claim 1, comprising administering 0.1 mg/kg to 5 mg/kg per day of ecopipam or a pharamaceutically acceptable salt thereof.

19. The method of claim 18, comprising administering ecopipam hydrochloride.

20. A method of treating Tourette's Disorder in a human patient in need thereof and not older than 18 years, comprising administering to the patient once daily oral dosages of ecopipam or a pharmaceutically acceptable salt thereof in a unit dosage form comprising 10 mg to 200 mg ecopipam or a pharmaceutically acceptable salt thereof.

21. A method of treating Tourette's Disorder in a human patient in need thereof and not older than 18 years, comprising administering to the patient once daily oral dosages of ecopipam or a pharmaceutically acceptable salt thereof at a daily dose in a range of about 0.1 mg/kg to about 5 mg/kg.

* * * * *

UNITED STATES PATENT AND TRADEMARK OFFICE
CERTIFICATE OF CORRECTION

| | | |
|---|---|---|
| PATENT NO. | : 11,298,361 B2 | Page 1 of 1 |
| APPLICATION NO. | : 14/414368 | |
| DATED | : April 12, 2022 | |
| INVENTOR(S) | : Chipkin et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 613 days.

Signed and Sealed this
Twenty-ninth Day of November, 2022

Katherine Kelly Vidal
*Director of the United States Patent and Trademark Office*